(12) United States Patent
Gmunder et al.

(10) Patent No.: US 6,531,114 B1
(45) Date of Patent: Mar. 11, 2003

(54) SILDENAFIL CITRATE CHEWING GUM FORMULATIONS AND METHODS OF USING THE SAME

(75) Inventors: Charlean B. Gmunder, Branchburg; Weisheng Li, Bridgewater, both of NJ (US); Ronald L Ream, Plano, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 150 days.

(21) Appl. No.: 09/714,571

(22) Filed: Nov. 16, 2000

Related U.S. Application Data (63) Continuation-in-part of application No. 09/621,780, filed on Jul. 21, 2000, which is a continuation of application No. PCT/US99/29792, filed on Dec. 14, 1999, application No. 09/714,571, which is a continuation-in-part of application No. 09/286,818, filed on Apr. 6, 1999.

(51) Int. Cl.[7] .......................... A61K 9/68; A61K 47/00; A61K 9/20; A61K 9/14
(52) U.S. Cl. ..................... 424/48; 424/439; 424/440; 424/464; 424/489
(58) Field of Search ................ 424/439, 440, 424/464, 48, 489; 514/929, 925, 866

(56) References Cited

U.S. PATENT DOCUMENTS

| | | | |
|---|---|---|---|
| 1,298,670 A | 4/1919 | Cramer | |
| 1,629,461 A | 5/1927 | Berg et al. | |
| 2,892,753 A | 6/1959 | Schmidt et al. | 167/65 |
| 2,990,328 A | 6/1961 | Lincoln | 167/55 |
| 3,011,949 A | 12/1961 | Bilotti | 167/82 |
| 3,029,189 A | 4/1962 | Hardy, Jr. et al. | 167/65 |
| 3,047,461 A | 7/1962 | Hardy, Jr. et al. | 167/65 |
| 3,075,884 A | 1/1963 | Bilotti et al. | 167/82 |
| 3,196,172 A | 7/1965 | Wright, Jr. et al. | 260/471 |
| 3,308,022 A | 3/1967 | Cummings et al. | 167/65 |

(List continued on next page.)

FOREIGN PATENT DOCUMENTS

| | | |
|---|---|---|
| DE | 43 42 568 | 6/1984 |
| EP | 0202819 A2 | 11/1986 |
| EP | 1217109 A2 | 4/1987 |
| EP | 0 221 850 | 5/1987 |
| EP | 0239541 A2 | 9/1987 |
| EP | 0371584 A2 | 6/1990 |
| EP | 0 273 809 | 7/1998 |
| FR | 2345938 | 3/1976 |
| FR | 2 635 441 | 2/1990 |
| FR | 2706771 | 6/1993 |
| GB | 0 934 596 | 8/1963 |

(List continued on next page.)

OTHER PUBLICATIONS

Merck Index, 12th Ed., #6977 "Omeprazole" (1996), p. 1174.
Merck Index, 12th Ed., #8272 "Raberprazole" (1996), p. 1392.
Merck Index, 12th Ed., #8286 "Ranitidine" (1996), p. 1395.
James G. Elliott, "Application of Antioxidant Vitamins in Foods and Beverges" Food Technology, (Feb. 1999), pp. 46–48.
C. Curtis Vreeland, "Nutraceuticals Fuel Confectionery Growth" Candy R&D, (Mar. 1999), pp. 29, 31–32, 34–35.
Kitty Broihier, R.D., "Foods of Tomorrow, Milking The Nutrition Market", Food Processing, (Mar., 1999), pp. 41, 42 and 44.

(List continued on next page.)

Primary Examiner—Thurman K. Page
Assistant Examiner—S. Howard
(74) Attorney, Agent, or Firm—Bell, Boyd & Lloyd LLC (57) ABSTRACT

Methods and chewing gum formulations for delivering a medicament, namely sildenafil citrate, to an individual are provided. Further, an improved dosage form and method of treating erectile dysfunction are provided. Methods of treating esophageal spasms, dysphagia, and gastroparesis utilizing chewing gum formulations containing sildenafil citrate are also provided.

33 Claims, 1 Drawing Sheet

U.S. PATENT DOCUMENTS

| | | | |
|---|---|---|---|
| 3,498,964 A | 3/1970 | Hayashi | 260/112 |
| 3,554,767 A | 1/1971 | Daum | 99/134 |
| 3,590,057 A | 6/1971 | Suzuki et al. | 260/404 |
| 3,845,217 A | 10/1974 | Ferno et al. | 426/3 |
| 3,877,468 A | 4/1975 | Lichtneckert et al. | 131/2 |
| 3,901,248 A | 8/1975 | Lichtneckert et al. | 131/2 |
| 3,995,064 A | 11/1976 | Ehrgott et al. | 426/3 |
| 4,154,814 A | 5/1979 | Hand et al. | 424/48 |
| 4,238,475 A | 12/1980 | Witzel et al. | 424/48 |
| 4,238,510 A | 12/1980 | Cherukuri et al. | 426/5 |
| 4,283,408 A | 8/1981 | Hirata et al. | 424/270 |
| 4,317,838 A | 3/1982 | Cherukuri et al. | 426/5 |
| 4,374,858 A | 2/1983 | Glass et al. | |
| 4,378,374 A | 3/1983 | Reggio et al. | |
| 4,386,063 A | 5/1983 | Boden | 424/49 |
| 4,386,106 A | 5/1983 | Merritt et al. | |
| 4,400,372 A | 8/1983 | Muhler et al. | 424/48 |
| 4,446,135 A | 5/1984 | Fountaine | 424/154 |
| 4,452,821 A | 6/1984 | Gergely | 426/5 |
| 4,459,311 A | 7/1984 | De Tora et al. | 426/3 |
| 4,474,749 A | 10/1984 | Kruppa | 424/48 |
| 4,512,968 A | 4/1985 | Komiyama et al. | 424/48 |
| 4,533,556 A | 8/1985 | Piccolo et al. | 426/3 |
| 4,555,407 A | 11/1985 | Kramer et al. | 426/5 |
| 4,563,345 A | 1/1986 | Arrick | 424/48 |
| 4,639,368 A | 1/1987 | Niazi et al. | 424/48 |
| 4,647,450 A | 3/1987 | Peters et al. | 424/48 |
| 4,711,774 A | 12/1987 | Denick, Jr. et al. | 424/48 |
| 4,716,033 A | 12/1987 | Denick, Jr. | 424/48 |
| 4,737,366 A | 4/1988 | Gergely et al. | 426/5 |
| 4,753,800 A | 6/1988 | Mozda | 424/440 |
| 4,753,805 A | 6/1988 | Cherukuri et al. | 426/5 |
| 4,755,389 A | 7/1988 | Jones et al. | 424/456 |
| 4,758,424 A | 7/1988 | Denick, Jr. et al. | 424/48 |
| 4,822,597 A | 4/1989 | Faust et al. | 424/48 |
| 4,822,816 A | 4/1989 | Markham | 514/474 |
| 4,828,820 A | 5/1989 | Glass et al. | 424/48 |
| 4,832,994 A | 5/1989 | Fey | 424/48 |
| 4,835,162 A | 5/1989 | Abood | 514/305 |
| 4,849,227 A | 7/1989 | Cho | 424/498 |
| 4,853,212 A | 8/1989 | Faust et al. | 424/48 |
| 4,867,989 A | 9/1989 | Silva et al. | 426/5 |
| 4,882,152 A | 11/1989 | Yang et al. | 424/440 |
| 4,894,234 A | 1/1990 | Sharma et al. | 426/5 |
| 4,908,211 A | 3/1990 | Paz | 424/440 |
| 4,908,212 A | 3/1990 | Kwon et al. | 424/440 |
| 4,929,447 A | 5/1990 | Yang | 424/440 |
| 4,929,508 A | 5/1990 | Sharma et al. | 424/439 |
| 4,933,184 A | 6/1990 | Tsuk | 424/449 |
| 4,935,242 A | 6/1990 | Sharma et al. | 424/439 |
| 4,938,963 A | 7/1990 | Parnell | 424/440 |
| 4,944,949 A | 7/1990 | Story et al. | 424/451 |
| 4,963,369 A | 10/1990 | Song et al. | 426/5 |
| 4,968,511 A | 11/1990 | D'Amelia et al. | 426/6 |
| 4,968,716 A | 11/1990 | Markham | 514/474 |
| 4,971,079 A | 11/1990 | Talapin et al. | 131/359 |
| 4,971,787 A | 11/1990 | Cherukuri et al. | 414/48 |
| 4,975,270 A | 12/1990 | Kehoe | 424/48 |
| 4,978,537 A | 12/1990 | Song | 426/5 |
| 4,997,659 A | 3/1991 | Yatka et al. | 426/3 |
| 5,013,716 A | 5/1991 | Cherukuri et al. | 514/23 |
| 5,015,464 A | 5/1991 | Strobridge | 424/48 |
| 5,045,325 A | 9/1991 | Lesko et al. | 426/5 |
| 5,070,085 A | 12/1991 | Markham | 514/161 |
| 5,110,608 A | 5/1992 | Cherukuri et al. | |
| 5,124,156 A | 6/1992 | Shibata et al. | 424/440 |
| 5,126,151 A | 6/1992 | Bodor et al. | |
| 5,139,787 A | 8/1992 | Broderick et al. | |
| 5,154,927 A | 10/1992 | Song et al. | |
| 5,156,842 A | 10/1992 | Mulligan | |
| 5,179,122 A | 1/1993 | Greene et al. | |
| 5,182,099 A | 1/1993 | Jonsson et al. | |
| 5,229,137 A | 7/1993 | Wolfe | 424/687 |
| 5,244,670 A | 9/1993 | Upson et al. | 424/439 |
| 5,284,657 A | 2/1994 | Lu et al. | |
| 5,286,500 A | 2/1994 | Synosky et al. | 426/3 |
| 5,294,433 A | 3/1994 | Singer et al. | |
| 5,294,449 A | 3/1994 | Greenberg | |
| 5,340,566 A | 8/1994 | Curtis et al. | |
| 5,378,131 A | 1/1995 | Greenberg | |
| 5,380,530 A | 1/1995 | Hill | |
| 5,380,535 A | 1/1995 | Geyer et al. | |
| 5,397,580 A | 3/1995 | Song et al. | 426/5 |
| 5,410,028 A | 4/1995 | Asami et al. | |
| 5,419,919 A | 5/1995 | Song et al. | 426/5 |
| 5,433,960 A * | 7/1995 | Meyers | 426/5 |
| 5,445,834 A | 8/1995 | Burger et al. | |
| 5,455,286 A | 10/1995 | Amidon et al. | |
| 5,456,677 A | 10/1995 | Spector | |
| 5,487,902 A | 1/1996 | Andersen et al. | |
| 5,488,962 A | 2/1996 | Perfetti | |
| 5,494,685 A | 2/1996 | Tyrpin et al. | |
| 5,496,541 A | 3/1996 | Cutler | |
| 5,512,306 A | 4/1996 | Carlsson et al. | |
| 5,523,097 A | 6/1996 | Song et al. | 426/3 |
| 5,534,272 A | 7/1996 | Bernstein | |
| 5,543,160 A | 8/1996 | Song et al. | 426/3 |
| 5,554,380 A | 9/1996 | Cuca et al. | |
| 5,569,477 A | 10/1996 | Nesbitt | 426/5 |
| 5,571,528 A | 11/1996 | Lee et al. | |
| 5,571,543 A | 11/1996 | Song et al. | 426/5 |
| 5,576,344 A | 11/1996 | Sandler et al. | 414/427 |
| 5,580,590 A | 12/1996 | Hartman | |
| 5,582,855 A | 12/1996 | Cherukuri et al. | |
| 5,585,110 A | 12/1996 | Kalili et al. | |
| 5,593,685 A | 1/1997 | Bye et al. | |
| 5,601,858 A | 2/1997 | Mansukhani et al. | |
| 5,605,698 A | 2/1997 | Ueno | |
| 5,607,697 A | 3/1997 | Alkire et al. | |
| 5,618,517 A | 4/1997 | Miskewitz | |
| 5,628,986 A | 5/1997 | Sanker et al. | |
| 5,629,013 A | 5/1997 | Davis | 424/441 |
| 5,629,026 A | 5/1997 | Davis | 424/686 |
| 5,629,035 A | 5/1997 | Miskewitz | |
| 5,645,853 A | 7/1997 | Winston et al. | |
| 5,651,987 A | 7/1997 | Fuisz | |
| 5,656,652 A | 8/1997 | Davis | 514/400 |
| 5,665,386 A | 9/1997 | Benet et al. | |
| 5,667,802 A | 9/1997 | Grimberg | |
| 5,693,334 A | 12/1997 | Miskewitz | |
| 5,698,215 A | 12/1997 | Kalili et al. | |
| 5,702,687 A | 12/1997 | Miskewitz | |
| 5,711,961 A | 1/1998 | Reiner et al. | |
| 5,716,928 A | 2/1998 | Benet et al. | |
| 5,736,175 A | 4/1998 | Cea et al. | |
| 5,744,164 A | 4/1998 | Chauffard et al. | |
| 5,753,255 A | 5/1998 | Chavkin et al. | |
| 5,756,074 A | 5/1998 | Ascione et al. | |
| 5,800,847 A | 9/1998 | Song et al. | 426/3 |
| 5,824,291 A | 10/1998 | Howard | |
| 5,834,002 A | 11/1998 | Athanikar | |
| 5,846,557 A | 12/1998 | Eisenstadt et al. | |
| 5,854,267 A | 12/1998 | Berlin et al. | 514/370 |
| 5,858,383 A | 1/1999 | Precopio | 424/405 |
| 5,858,412 A | 1/1999 | Staniforth et al. | 424/489 |
| 5,858,413 A | 1/1999 | Jettka et al. | 424/682 |
| 5,858,423 A | 1/1999 | Yajima et al. | 426/3 |
| 5,866,179 A | 2/1999 | Testa | |
| 5,877,173 A | 3/1999 | Olney et al. | |

| | | |
|---|---|---|
| 5,882,702 A | 3/1999 | Abdel-Malik et al. |
| 5,889,028 A | 3/1999 | Sandborn et al. ............ 514/343 |
| 5,889,029 A | 3/1999 | Rolf |
| 5,897,891 A | 4/1999 | Godfrey |
| 5,900,230 A | 5/1999 | Cutler |
| 5,912,007 A | 6/1999 | Pan et al. |
| 5,912,030 A | 6/1999 | Huziinec et al. |
| 5,916,606 A | 6/1999 | Record et al. |
| 5,922,346 A | 7/1999 | Hersh |
| 5,922,347 A | 7/1999 | Hausler et al. |
| 5,928,664 A | 7/1999 | Yang et al. |
| 5,958,380 A | 9/1999 | Winston et al. |
| 5,958,472 A | 9/1999 | Robinson et al. |
| 5,980,955 A | 11/1999 | Grennberg et al. ............ 426/5 |
| 5,989,588 A | 11/1999 | Korn et al. ................. 424/465 |
| 6,024,988 A | 2/2000 | Ream et al. .................... 426/3 |
| 6,066,988 A | 5/2000 | Gurol et al. ............... 424/687 |
| 6,077,524 A | 6/2000 | Bolder et al. |
| 6,090,412 A | 7/2000 | Hashimoto et al. ......... 424/490 |
| 6,165,516 A | 12/2000 | Gudas et al. |
| 6,221,402 B1 * | 4/2001 | Itoh et al. ................... 424/494 |

FOREIGN PATENT DOCUMENTS

| | | |
|---|---|---|
| GB | 0 963 518 | 7/1964 |
| GB | 1 489 832 | 10/1977 |
| GB | 2181646 A | 4/1987 |
| GB | 94-2868 | 4/1994 |
| IT | 0217487 | 7/1997 |
| JP | 91-112450 | 9/1989 |
| JP | 91-251533 | 11/1991 |
| JP | 94-303911 | 11/1994 |
| JP | 96-19370 | 1/1996 |
| JP | 86/242561 | 10/1996 |
| WO | 84/02271 | 6/1984 |
| WO | 90/12511 | 11/1990 |
| WO | 90/12583 | 11/1990 |
| WO | 92/06680 | 4/1992 |
| WO | 95/00038 | 1/1995 |
| WO | 95/00039 | 1/1995 |
| WO | 95/10290 | 4/1995 |
| WO | 96/00070 | 1/1996 |
| WO | 96/03975 | 2/1996 |
| WO | 97/21424 | 6/1997 |
| WO | WO 97/24036 | 7/1997 |
| WO | 98/23165 | 6/1998 |
| WO | 98/23166 | 6/1998 |
| WO | 98/23167 | 6/1998 |
| WO | 99/33352 | 7/1999 |
| WO | 99/44436 | 9/1999 |
| WO | 00/13523 | 3/2000 |
| WO | 00/35296 | 6/2000 |
| WO | 00/35298 | 6/2000 |
| WO | 00/38532 | 7/2000 |

OTHER PUBLICATIONS

Kitty Broihier, R.D., "Tea Time For Nutraceuticals, New Black, Green Tea Products Brew Up a Bevy Of Health Benefits", Food Processing: (Mar., 1999), pp. 59, 61 and 63.
Andrea Allen, Jack Neff, Lori Dahm and Mary Ellen Kuhn, "Exclusive Guide to Wellness Foods and Nutraceuticals", Food Processing (Special Suplement), (Mar., 1999).
Product package "Aspergum" distributed by Heritage Consumer Products, LLC (on sale prior to Nov. 27, 1995).
Product package "Chew & Sooth Zinc Dietary Supplement Gum" by Gumtech International, Inc. (undated).
Product package "Dental Care the Baking Soda Gum" distributed by Church & Dwight Co., Inc. (1998).
Product package "BreathAsure Dental Gum" distributed by Breath Asure, Inc. (1998).
Product package "Trident Advantage with Baking Soda" distributed by Warner–Lambert Co. (1998).
Product package "CHOOZ Antacid/Calcium Supplement with Calcium Carbonate" distributed by Heritage Consumer Products Co.
Hertiage Consumer Products Co. article from the Internet "Cosmetics and Toiletries, The Heritage Story", printed Jul. 20, 2000,<http://www.enewsusa.com/Connecticut/14997.html>, 1 page.
The United States Pharmacopeia The National Formulary—"General Information", dated Jan. 1, 1990 pp 1624–1625 and pp 1696–1697.
Gumtech article from the Internet "Customized Solutions For Customer Brands", printed Oct. 18, 2000,<http://www.gum–tech.com/cus–brands.html>, 3 pages.
Product package for Stay Alert Caffeine Supplement Gum, distributed by Amurol Confections Company (first quarter 1998).
Rabeprazole article from the Internet "Rabeprazole: Pharmacokinetics and Safety in the Elderly", printed Sep. 22, 2000,<http://www.mmhc.com/cg/articles/CG9905/Hum–phries.html>, 2 pages.
"Flavor Encapsulation Technologies, Flavor Unit Sweet, Product Management", H&R (undated) (published at least before Nov. 27, 1996), 25 pages.
Dr. Massimo Calanchi and Dr. Sam Ghanta, "Taste–masking of oral formulations", Eurand International SpA, Pharmaceutical, Manufacturing International, 1996 (5 pages).
The Eurand Group, Brochure (undated) (published at least before Nov. 27, 1996), (16 pages).
Merck Index, 11th Ed. #1635 "Caffeine" (1989), p. 248.
Merck Index, 12th Ed., #2337 "Cimetidine" (1996), p. 383.
Merck Index, 12th Ed., #3264 "Dimethicone" (1996), p. 544.
Merck Index, 12th Ed., #3972 "Famotidine" (1996), p. 667.
Merck Index, 12th Ed., #6758 "Nizatidine" (1996), p. 1143.
U.S. patent application Ser. No. 09/286,818, Ream et al., filed Apr. 6, 1999.
U.S. patent application Ser. No. 09/421,905, Ream et al., filed Oct. 20, 1999.
Specialty Minerals Inc. Brochure (Apr. 1998), (19 pages).
U.S. patent application Ser. No. 09/510,878, Ream et al., filed Feb. 23, 2000.
U.S. patent applicaton Ser. No. 09/535,458, Ream et al., filed Mar. 24, 2000.
U.S. patent application Ser. No. 09/552,290, Song et al., filed Apr. 19, 2000.
U.S. patent application Ser. No. 09/591,256, Zyck et al., filed Jun. 9, 2000.
U.S. patent application Ser. No. 09/592,400, Ream et al., filed Jun. 13, 2000.
U.S. patent application Ser. No. 09/618,808, Ream et al., filed Jul. 18, 2000.
U.S. patent application Ser. No. 09/621,643, Johnson et al., filed Jul. 21, 2000.
U.S. patent application Ser. No. 09/621,780, McGrew et al., filed Jul. 21, 2000.
U.S. patent application Ser. No. 09/631,326, Ream et al., filed Aug. 3, 2000.
U.S. patent application Ser. No. 09/651,514, Tyrpin et al., filed Aug. 30, 2000.
U.S. patent application Ser. No. 09/653,669, Zyck et al., filed Sep. 1, 2000.

U.S. patent application Ser. No. 09/654,464, Zyck et al., filed Sep. 1, 2000.
U.S. patent application Ser. No. 09/671,552, Ream et al., filed Sep. 27, 2000.
U.S. patent application Ser. No. 09/681,935, Seielstad et al., filed Jun. 28, 2001.
U.S. patent application Ser. No. 09/747,300, Zyck et al., filed Dec. 22, 2000.
U.S. patent application Ser. No. 09/747,323, Zyck et al., filed Dec. 22, 2000.
U.S. patent application Ser. No. 09/748,699, Zyck et al., filed Dec. 22, 2000.
U.S. patent application Ser. No. 09/749,983, Urnezis et al., filed Dec. 27, 2000.
U.S. patent application Ser. No. 09/759,561, Ream et al., filed Jan. 11, 2001.
U.S. patent application Ser. No. 09/759,838, Ream et al., filed, Jan. 11, 2001.
U.S. patent application Ser. No. 09/924,914, Ream et al., filed Aug. 8, 2001.
Akitoshi et al., Abstract "Acceleration of Transdermal Absorption of Pharmaceuticals by Essential Oils and Organic Solvents," Chem. Abst., 112:125228t, 1990.
Bradford, A Rapid and Sensitive Method for the Quantification of Microgram Quantities of Protein Utilizing the Principle of Protein–Dye Binding, Analytical Biochemistry, 72:248–254 (1976).
Nielsen et al., P–Glycoprotein as Multidrug Trnasporter: A Critical Review of Current Multidrug Resistant Cell Lines, Chimica et Biophysica Acta., 1139: 169–183 (1992).
Adams, M.W., d–Alpha Tocopheryl Polyethylene glycol 1000 succinate (Eastman vitamin E TPGS) as an Emulsifier and Bioenhancer for Drugs and Lipophilic Compounds, 6th International Conference on Pharmaceutical Technology, Paris, Jun. 2–4, 1992.
Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.
Hebert, Mary F. et al.; "Bioavailability of Cyclosporine with Concomitant Rifampin Administration is Markedly Less Than Predicted by Hepatic Enzyme Induction" (1992) Clin. Pharmacol. Ther. 52:453–457.

Kronbach, Thomas et al.; "Oxidation of Midazolam and Triazolam by Human Liver Cytochrome P450IIIA4" (1989) Molec. Pharm. 36:89–96.

Lalka et al.,: "The Hepatic First–Pass Metabolism of Problematic Drugs" (1993) J. clin. Pharmacol. 33:657–669.

Lum et al.; "Clinical Trials of Modulation of Multidrug Resistance. Pharmacokinetic and Pharmacodynamic Considerations" (1993) Cancer 72:3502–3514.

Muranishi, Shozo; "Absorption Enhancers" (1990) Crit. Rev. Ther. Drug Carrier Sys., 7:1–33.

Somberg et al.; "The Clinical Implications of First–Pass Metabolism: Treatment Strategies for the 1990's" (1993) J. Clin. Pharmacol. 33:670–673.

Tam, Yun K.; "Individual Variation in First–Pass Metabolism" (1993) Clin. Pharmacokinet. 25:300–328.

Van Hoogdalem et al.; "Intestinal Drug Absorption Enhancement: An Overview" (1989) Pharmacol. Ther. 44:407–443.

Warren et al.; "Increased Accumulation of Drugs in Multidrug–Resistant Cell Induced by Liposomes" (1992) Cancer Research 52:3241–3245.

Watkins, Paul B; "The Role of Cytochromes P–450 in Cyclosporine Metabolism" (1990) J.Am. Acad. Dermacol. 23:1301–1309.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption an d Metabolism" (1993) Pharm. Res. 10: abstract ppdm8185.

Zamora et al.; "Physical–Chemical Properties Shared by Compounds that Modulate Multidrug Resistance in Human Loukemic Cells" (1988) Molec. Pharmacol. 33:454–462.

* cited by examiner

Figure 1

SILDENAFIL CITRATE CHEWING GUM FORMULATIONS AND METHODS OF USING THE SAME

This application is a continuation-in-part patent application of U.S. patent application Ser. No. 09/286,818, filed on Apr. 6, 1999, entitled "Pharmaceutical Chewing Gum Formulation", and U.S. patent application Ser. No. 09/621,780 filed on Jul. 21, 2000 which is a continuation and claims priority from PCT patent application PCT/US99/29792 filed Dec. 14, 1999 now WO 00/35298 entitled "Chewing Gum Containing Medicament or Other Active Agents."

BACKGROUND OF THE INVENTION

The present invention generally relates to medicaments and other agents. More specifically, the present invention relates to the delivery of medicaments or other agents.

It is of course known to provide agents to individuals for various purposes. There are a great variety of such agents. These agents can be used to treat diseases and as such are typically referred to as drugs or medicaments. Likewise, the drugs or medicaments can be used for prophylactic purposes. In addition, some agents are taken on an as needed basis while others must be taken at regular intervals by the individual being treated.

Still, it is known to provide such agents to an individual for a variety of indicated medicinal purposes such as sildenafil citrate for the treatment of male erectile dysfunction. Typically, drugs (medicaments) are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation. Except when given intravenously, a drug must traverse several semi-permeable cell membranes before reaching general circulation. These membranes act as a biological barrier that inhibits the passage of drug molecules. There are believed to be four processes by which drugs move across a biological barrier: passive diffusion; facilitated diffusion; active transport; and pinocytosis.

Passive diffusion is the transport across the cell membrane wherein the driving force for the movement is the concentration gradient of the solute. In orally administered drugs, this absorption occurs in the small intestines. Facilitated diffusion is believed to be based on a carrier component that combines reversibly with the substrate molecule at the cell membrane exterior. The carrier substrate complex diffuses rapidly across the membrane with release of the substrate at the interior surface. Active transport requires an energy expenditure by the cell and appears to be limited to agents with structural similarities to normal body constituents. These agents are usually absorbed from specific sites in the small intestines. Pinocytosis refers to the engulfing of particles or fluid by a cell. It is believed to play a minor role in drug transport. *Merck Manual*, 16th Edition, pp. 2598–2599.

In determining the efficacy of a drug and the effectiveness of the use of a drug to treat a disease, drug absorption is a critical concern. Drug absorption refers to the process of drug movement from the site of administration toward the systemic circulation.

Oral administration of drugs is by far the most common method. When administered orally, drug absorption usually occurs due to the transport of cells across the membranes of the epithelial cells within the gastrointestinal tract. Absorption after oral administration is confounded by numerous factors. These factors include differences down the alimentary cannel in: the luminal pH; surface area per luminal volume; perfusion of tissue, bile, and mucus flow; and the epithelial membranes. See *Merck Manual* at page 2599.

In particular, oral transmucosal administration via the sublingual or buccal routes is generally quite rapid because of the rich vascular supply within the oral mucosa. The oral cavity exhibits a minimal barrier to drug transport and results in a rapid rise in blood concentrations.

In addition, for significant drug absorption to occur across the oral mucosa, the drug must have a prolonged exposure to the mucosal surface. Taste, then, is one of the major determinants of contact time with the oral mucosa. Such is the case with most medicaments. Sildenafil citrate, for example, exhibits a bitter taste. *Physician's Desk Reference*, 23$^{rd}$ edition, Page 2424.

A further issue effecting the absorption of orally administered drugs is the form of the drug. Most orally administered drugs are in the form of tablets or capsules. This is done primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that effect the dissolution rate and therefore determine the availability of the drug for absorption. See *Merck Manual* at page 2600.

Sildenafil citrate, in particular, is the effective ingredient in Viagra® tablets manufactured by Pfizer Inc. Although the tableted dosage form of sildenafil citrate has been proven very effective for male erectile dysfunction, such a dosage form has shown certain side effects. For instance, some patients taking Viagra® tablets experienced gastroesophageal reflux (a regurgitation of food from the stomach). A gradual release dosage form of sildenafil citrate might prove to be gentler to the stomach and enhance the desirability of the drug to a larger patient population requiring its use.

Not only is drug absorption a central issue in drug delivery, but also the bioavailability of the drug as well. Bioavailability is defined as the rate at which and the extent to which the active moiety (drug or metabolite) enters the general circulation, thereby gaining access to the site of action. Bioavailability depends upon a number of factors, including how a drug product is designed and manufactured, its physiochemical properties, and factors that relate to the physiology and pathology of the patient. See *Merck Manual* at page 2602.

When a drug rapidly dissolves from a dosage form and readily passes across membranes, absorption from most administration sites tends to be complete. This is not always the case for drugs given orally. Before reaching the vena cava, the drug must move down the alimentary cannel and pass through the gut wall and liver, which are common sites of drug metabolism. Thus, the drug may be metabolized before it can be measured in the general circulation. This can cause a decrease in the amount of drug available to exert a therapeutic effect called the first pass effect.

A large number of drugs show low bioavailabilities owing to an extensive first pass metabolism. The two other most frequent causes of low bioavailability are insufficient time in the oral cavity, or GI tract and the presence of competing reactions. See *Merck Manual* at page 2602. Bioavailability considerations are most often encountered for orally administered drugs. Differences in bioavailability can have profound clinical significance. Sildenafil citrate, for example, exhibits only a 40% bioavailability after oral administration, of which the active metabolite accounts for about one-half. *Physician's Desk Reference,* at 2425.

Therefore, there is a need for an improved sildenafil or derivative thereof formulation and method of delivering the same to an individual requiring its use, which overcomes the absorption, bioavailability, and gastroesophageal problems noted above as well as other needs.

SUMMARY OF THE INVENTION

The present invention provides improved methods and delivery vehicles, i.e., dosage forms, for delivering sildenafil or derivatives thereof to an individual requiring its use. To this end, chewing gum is provided as a dosage form that contains sildenafil, preferably sildenafil citrate. The sildenafil citrate component is present within the chewing gum composition (the water soluble portion and/or insoluble base portion). It has been found that by chewing the chewing gum composition of the present invention, the drug is gradually released from the chewing gum. Continuing to chew the chewing gum creates a pressure within the oral cavity of the individual to force sildenafil citrate directly into the systemic system of that individual through the oral mucosa of the oral cavity via the buccal or sublingual absorption routes. This gradual release of sildenafil citrate by the chewing gum composition of the present invention greatly enhances the drug's absorption and bioavailability within the systemic system, prolongs the therapeutic effect of the drug due to more of the drug being available to exert such an effect over an extended period of time, and reduces or eliminates the gastroesophageal reflux side effect associated with the drug.

To this end, the present invention provides a chewing gum composition containing sildenafil powder or a derivative thereof and a method of delivering the same comprising the steps of: providing a chewing gum composition that includes sildenafil, preferably sildenafil citrate, in the chewing gum composition; chewing the chewing gum composition to cause the drug to be gradually released from the composition into the oral cavity of the chewer, and continuing to chew the composition thereby creating a fluid pressure causing the drug to enter the systemic system of the chewer through the oral mucosa of the oral cavity via the buccal or sublingual absorption routes.

In an embodiment of the composition, the chewing gum is chewed for at least 2 minutes.

In an embodiment of the composition, the chewing gum contains sildenafil citrate.

In an embodiment of the composition, the particle size of sildenafil, preferably sildenafil citrate, powder incorporated into the chewing gum composition is approximately 0.1 microns to about 200 microns in diameter, more preferably from about 0.1 microns to about 50 microns in diameter.

In an embodiment of the composition, each piece of the chewing gum contains approximately 5 mg to about 100 mg of pure sildenafil citrate.

In an embodiment, the chewing gum includes an outer coating and the sildenafil is incorporated, at least partially, in the coating.

In an embodiment, the chewing gum comprises a coating that surrounds a dextrose center.

In a further embodiment, the present invention provides a method of delivering sildenafil citrate in the treatment of male erectile dysfunction comprising the steps of: providing chewing gum including a therapeutically effective amount of sildenafil citrate to treat male erectile dysfunction; and chewing the gum for at least 2 minutes.

In an embodiment of the method, the chewing gum composition is chewed at least 30 minutes prior to engaging in a sexual activity.

In an embodiment of the method, the effective amount of sildenafil citrate to treat male erectile dysfunction is approximately 20 mg to about 100 mg of pure sildenafil citrate.

In a further embodiment, the present invention provides a method of delivering sildenafil citrate in the treatment of gastroparesis comprising the steps of: providing chewing gum including a therapeutically effective amount of sildenafil citrate to treat gastroparesis associated with diabetes and chewing the gum for at least 2 minutes.

In an embodiment of the method, the therapeutically effective amount of sildenafil citrate to treat gastroparesis associated with diabetes is approximately 5 mg to about 100 mg of pure sildenafil citrate.

In a still further embodiment, the present invention provides a method of delivering sildenafil citrate in the treatment of esophageal spasms and dysphagia comprising the steps of: providing chewing gum including a therapeutically effective amount of sildenafil citrate to treat esophageal spasms and dysphagia; and chewing the gum for at least 2 minutes.

In an embodiment of the method, the therapeutically effective amount of sildenafil citrate to treat esophageal spasms and dysphagia is approximately 5 mg to about 100 mg of pure sildenafil citrate.

In another embodiment, the present invention provides a method for reducing or eliminating the gastroesophageal reflux side effect associated with sildenafil citrate comprising the steps of: providing a chewing gum composition that contains sildenafil citrate; chewing the chewing gum causing the sildenafil citrate to be gradually released from the chewing gum; and continuing to chew the chewing gum to gradually force the drug through the mucous membranes of the oral cavity of an individual to enter the systemic system via the buccal or sublingual absorption routes.

Accordingly, an advantage of the present invention is to provide chewing gum formulations and methods for delivering sildenafil, preferably sildenafil citrate, to an individual.

Further, an advantage of the present invention is to provide a method of delivering sildenafil, preferably sildenafil citrate, to an individual via a delivery vehicle or dosage form i.e., chewing gum, that provides for increased absorption and bioavailability of the drug as compared to other oral dosage forms for sildenafil.

Moreover, an advantage of the present invention is to provide a method for orally delivering sildenafil citrate to an individual that is more palatable than current oral delivery methods.

Furthermore, an advantage of the present invention is to provide an improved method for delivering sildenafil citrate that reduces or eliminates the drug's gastroesophageal reflux side effect.

Still a further advantage of the present invention is to provide an improved method of treating male erectile dysfunction.

An additional advantage of the present invention is to provide a method of treating esophageal spasms and dysphagia.

Further, an advantage of the present invention is to provide a method of treating gastroparesis associated with diabetes.

Additional features and advantages of the present invention will be described in and apparent from the detailed description of the presently preferred embodiments and the figures.

DETAILED DESCRIPTION OF THE PRESENTLY PREFERRED EMBODIMENTS

Figure 1:
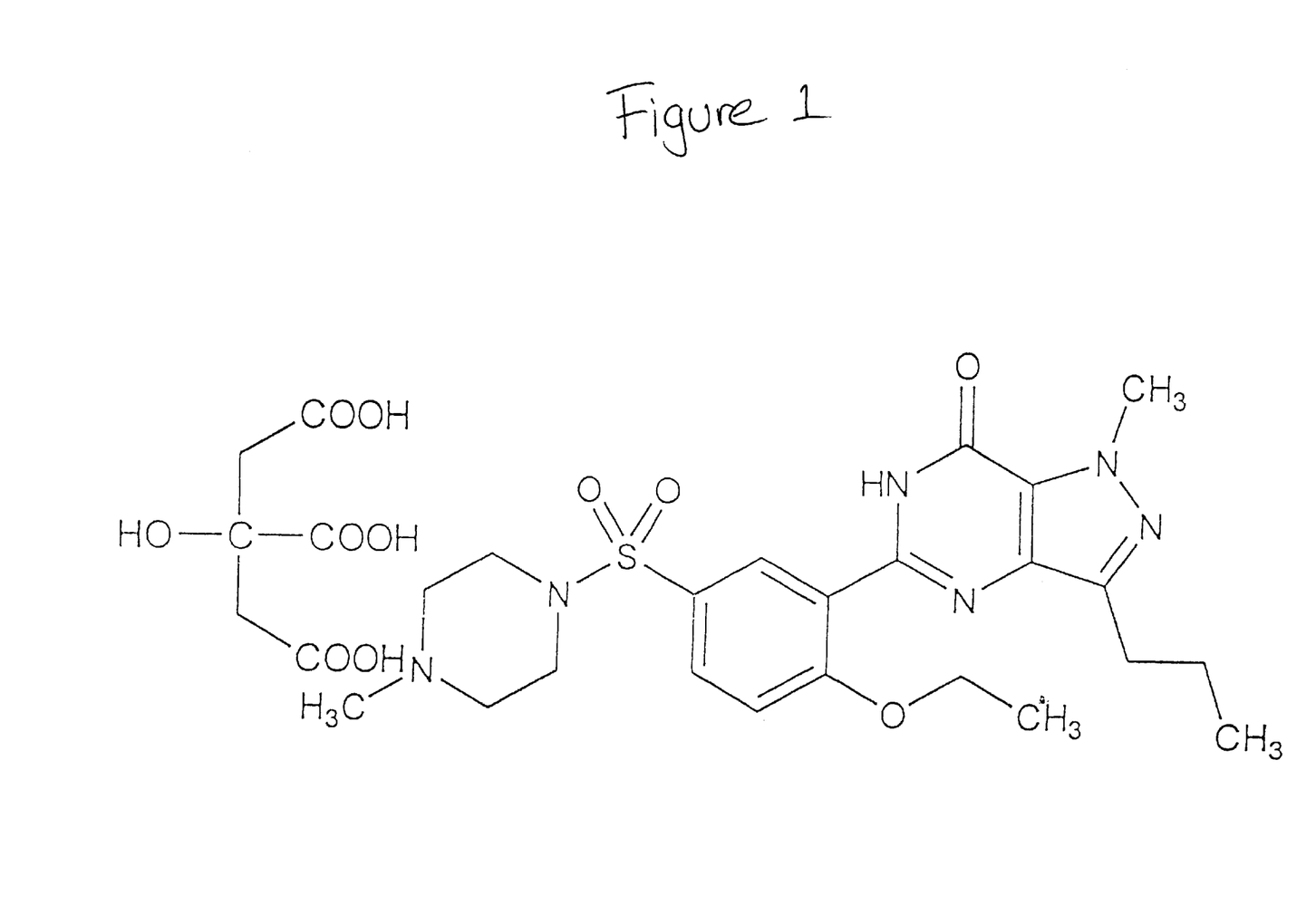
FIG. 1 illustrates graphically the chemical structure of sildenafil citrate that is discussed supra.

The present invention provides chewing gum compositions containing a medicament and methods for delivering the medicament, in particular sildenafil or a derivative thereof, preferably sildenafil citrate, to an individual. Pursuant to the present invention, sildenafil citrate is contained in the chewing gum composition.

Accordingly, as the chewing gum composition is chewed, the medicament is gradually released from the composition and into the saliva of the oral cavity. During continual chewing, the medicament in the saliva is then forced due to the pressure created by the chewing action through the oral mucosa of the oral cavity into the systemic circulation via the buccal or sublingual absorption routes. The oral mucosa has a thin epithelium and a rich vascularity. Thus, the oral mucosa favors rapid drug absorption. In contrast to a typical orally ingested drug wherein the solution is in contact too briefly with the oral mucosa for absorption to be appreciable, it is believed that during chewing, the agent and/or medicament remains in contact with the oral cavity for a longer period of time and is forced through the oral mucosa to a larger extent. In doing so, a larger portion of the drug is made available for rapid absorption without first pass effect to the general circulation unlike drugs orally ingested drugs from the stomach or small intestines of the gastrointestinal tract.

Further, it has also been surprisingly found that by masking the unpleasant taste of sildenafil citrate, within a chewing gum composition of the present invention, the composition causes an individual to retain the drug in the oral cavity for a longer period of time, again increasing the drug's contact time within that cavity. By masking sildenafil citrate's unpleasant taste, patient acceptance of the drug's oral administration is greatly enhanced.

Moreover, it has been surprisingly found that placement of sildenafil citrate within a chewing gum composition, i.e., dosage form, and gradually releasing the medicament from the chewing gum composition reduces or eliminates the gastroesophageal reflux side effect associated with the drug when incorporated into other oral dosage forms such as tablets. Although not wanting to be bound to any particular theory, it is believed that the gradual release of sildenafil citrate from the chewing gum composition prevents excessive concentrations of the drug from developing within the gastrointestinal tract, in particular the stomach, which in turn reduces or prevents the gastroesophageal reflux side effect.

It has also been surprisingly found that placement of a therapeutically effective amount of sildenafil citrate within a chewing gum composition is an effective method of delivering and treating male erectile dysfunction. By chewing the chewing gum composition to gradually release sildenafil citrate within the oral cavity, the therapeutic effect of the drug is prolonged over an extended period of time.

Additionally, it has also been surprisingly found that placement of a therapeutically effective amount of sildenafil citrate within a chewing gum composition is an effective method of delivering and treating gastroparesis associated with diabetes. Again, not wanting to be bound to any particular theory, it is believed that the gradual release of sildenafil citrate from the chewing gum composition diminishes the bloating, vomiting, loss of appetite, and dehydration effects associated with gastroparesis by relaxing the smooth muscle tissue of the gastrointestinal tract.

Further, it has also been surprisingly found that placement of a therapeutically effective amount of sildenafil citrate within a chewing gum composition is an effective method of delivering and treating esophageal spasms and dysphagia. Dysphagia is the medical condition in which a patient has difficulty in swallowing due to abnormal musculatory actions within the oral and esophageal regions of the gastrointestinal tract. It is believed that gradual release of sildenafil citrate from a chewing gum composition of the present invention causes a relaxatory effect upon the smooth muscle tissues of these regions, which in turn decreases their spasticity. In doing so, a more normal swallowing and peristaltic function can be achieved.

Preferably, the form of sildenafil contained within the chewing gum formulations is sildenafil citrate. The effective amount of sildenafil citrate contained within the chewing gum compositions is approximately 5 mg to 100 mg of pure sildenafil citrate per piece of chewing gum. For example, a typical piece of chewing gum according to the present invention weighs about 1 to about 3 grams total and would contain approximately 5 mg to about 100 mg of pure sildenafil citrate as a portion of that particular total. Thus, one serving of sildenafil citrate would be one piece of the chewing gum composition.

Due to the adverse events that have been associated with overdosage of sildenafil citrate, it is preferable that the number of servings of the chewing gum composition be limited to a total of 100 mg of sildenafil citrate per patient per day. The level of medicament or agent in the chewing gum formulation is selected so as to create, when the gum is chewed, a sufficiently high concentration of the medicament or agent in the saliva to exert the necessary therapeutic effect. It should be appreciated by one of ordinary skill in the art that the dose of sildenafil citrate within the chewing gum composition of the present invention can be adjusted to produce the necessary therapeutic effect for a variety of medical conditions such as male erectile dysfunction, gastroparesis, esophageal spasms, and dysphagia.

It should also be appreciated that one of ordinary skill within the art will be able to adjust the dosing regimen of the present invention to achieve the necessary therapeutic effect for a particular patient. For example, the dosing regimen of the chewing gum composition of the present invention is administered at least twice a day for the treatment of esophageal spasms, dysphagia, and gastroparesis. However, the dosing regimen may need to be adjusted based upon the particular therapeutic needs of a patient as well as that patient's renal and hepatic function. One of ordinary skill in the art will be able to appreciate such patient specific dosing regimen adjustments of the present invention.

For example, it is anticipated that a patient being treated for erectile dysfunction with the chewing gum of the present invention could chew at least one piece of the chewing gum containing approximately 20 mg to about 100 mg of sildenafil citrate approximately 1 hour before engaging in a sexual activity to achieve the desired erectile effect. However, it is also anticipated that the same patient could chew the chewing gum anywhere from 0.5 hours to 4 hours before engaging in the sexual activity to achieve the same desired erectile effect.

In addition, it is anticipated that a patient being treated for esophageal spasms, dysphagia, or gastroparesis associated with diabetes could chew at least at least one piece of the chewing gum of the present invention containing approximately 5 mg to about 100 mg of sildenafil citrate approximately twice a day. However, based upon the clinical response and functioning of that particular patient, the chewing gum composition could be chewed anywhere from once a day to more than twice a day to achieve the desired therapeutic effect in treating these conditions.

The medicament or agent of the present invention can be contained in a variety of different chewing gum compositions. The chewing gum can be a number of different structures. For example, the chewing gum can be a single piece, for example, a stick, slab, or other unitary structure.

On the other hand, the chewing gum can comprise an over-coated formulation. In this regard, if desired, the sildenafil can be located within a coating or shell that substantially encloses a gum center. The coating can comprise, in an embodiment, approximately 40 to about 75% of the chewing gum composition. In addition to the sildenafil, the coating can include a masking agent to improve the taste of the coating containing the sildenafil. A variety of masking agents can be utilized including: sucralose; zinc gluconate; ethyl maltol; glycine; acesulfame-k; aspartame; saccharin; fructose; xylitol; spray dried licorice root; glycerrhizine; dextrose; sodium glutonate; glucono delta-lactone; ethyl vanillin; vanillin; normal and high potency sweeteners; and a variety of appropriate flavors. A sufficient masking agent is used to mask the taste of the sildenafil. If desired, more than one masking agent can be used.

A variety of methods can be used for creating a coated chewing gum. For example, the coating can be applied in a three phase operation to a chewing gum center. In the first phase, a crude coating of an alternate application of syrup and powder is applied to the center. This is followed by a second phase called the finishing coating in which a fine powder and longer tumbling is used to produce a smooth finish. Finally, a shellacking and polishing third phase is performed to provide a high sheen, smooth finish. If desired, the second and third phases can be eliminated. The coating can surround a variety of different types of gum center compositions as set forth below.

In another embodiment of the present invention, a compressible excipient is tableted and then coated with a chewing gum product including the sildenafil. The tableted excipient can comprise, by way of example and not limitation, dextrose, sucrose, or other saccharides, sorbitol, mannitol, isomalitol, other compressible sugar alcohols or combinations thereof. The tableted compressible excipient is substantially surrounded by a gum coating. The coating includes the sildenafil and, in an embodiment, comprises at least 50% by weight of the product. Additionally, the coating can include a masking agent and the chewing gum.

Referring now to the chewing gum of the present invention, the chewing gums can be low or high moisture, sugar or sugarless, wax containing or wax free, low calorie (via high base or low calorie bulking agents), and/or may contain other dental and/or medicinal agents.

In general, a chewing gum typically comprises a water-soluble bulk portion, a water-insoluble chewable gum base portion, and a flavoring agent. The water-soluble portion dissipates with a portion of the flavoring agent over a period of time during chewing. The gum base portion is retained in the mouth throughout the chew. The term chewing gum refers to both a chewing and bubble gum in its general sense.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 15% to about 35%, by weight, of the chewing gum.

In an embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Elastomers provide the rubbery, cohesive nature of the gum, which varies depending on this ingredient's chemical structure and how it is compounded with other ingredients. Synthetic elastomers may include, but are not limited to, polyisobutylene, isobutylene-isoprene copolymer (butyl rubber), styrene-butadiene, copolymers having styrene-butadiene ratios of about 1:3 to about 3:1, polyvinyl acetate, vinyl acetate vinyl laurate copolymer having a vinyl laurate content of about 5% to about 50% by weight of the copolymer, and combinations thereof.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum. Preferred natural elastomers include jelutong, chicle, sorva and massaranduba balata.

Elastomer plasticizers may include, but are not limited to, rosin esters such as glycerol esters of rosin, methyl esters of rosin, pentaerythritol esters of rosin; terpene resins derived from alpha-pinene, beta-pinene, and/or d-limonene; and any suitable combinations of the foregoing. The resin tackifiers regulate the cohesiveness and tackiness of the final gums. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof. Fillers modify the texture of the gum base. The fillers can also be organic powders such as polyethylene, oat fiber, wood fiber, apple fiber, zein, gluten, gliadin, casein, and the like. Sildenafil citrate powder can be added as a filler during base making to achieve better encapsulation which may result in longer sildenafil release.

Softeners/emulsifiers may include tallow, hydrogenated tallow, hydrogenated and partially hydrogenated vegetable oils, cocoa butter, glycerol monostearate, glycerol triacetate, lecithin, non-hydrogenated, partially hydrogenated and fully hydrogenated mono-, di- and tri-glycerides from cottonseed, soybean, palm, palm kernel, coconut, and safflower sources, and other medium chain triglycerides, acetylated monoglycerides, fatty acids (e.g. stearic, plasmatic, oleic and linoleic acids), and combinations thereof. Such softeners/emulsifiers modify the texture of the gum base by introducing sharp melting transition during chewing.

Colorants and whiteners may include FD&C-type dyes and lakes, fruit and vegetable extracts, titanium dioxide, and combinations thereof. Colorants impart characteristics and remove or mask undesired characteristics in the chewing gum formulation.

The gum base may or may not include wax. An example of a wax-free gum base is disclosed in U.S. Pat. No. 5,286,500, the disclosure of which is incorporated herein by reference. Waxes aid in the curing of gum bases and in improving shelf life and texture of the final gum product. Wax crystal also improve the release of flavor from the final product.

Such gum bases are typically prepared by adding an amount of the elastomer, resin tackifier or softer, and filler to a pre-heated sigma blade mixer having a temperature of from about 50° F. to about 240° F. The initial amounts of ingredients comprising the initial mass of the insoluble gum base may be determined by the working capacity of the mixing kettle in order to attain a proper consistency and by the degree of compounding desired to break down and soften the elastomer. The longer the period of time compounding and use of lower molecular weight or softening point gum base ingredients, a lower viscosity and firmness will result in the final gum base.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, medicaments, and other components that provide desired attributes.

Softeners are added to the chewing gum in order to optimize the chewability and mouth feel of the gum. The softeners, which are also known as plasticizers and plasticizing agents, generally constitute between approximately 0.5% to about 25% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. The range of these sweeteners in chewing gum formulations typically can range from about 0.02 to about 0.10 weight percent for alitame, thaumatin and dihydrochalcones, and from about 0.1 to about 0.2 weight percent for aspartame, sucralose, acesulfame and saccharin.

In order to provide longer lasting sweetness and flavor perception, it may be desirable to encapsulate or otherwise control the release of at least a portion of the artificial sweetener. Techniques such as wet granulation, wax granulation, spray drying, spray chilling, fluid bed coating, coacervation, and fiber extension may be used to achieve the desired release characteristics.

Combinations of sugar and/or sugarless sweeteners may be used in the chewing gum. Additionally, the softener may also provide additional sweetness such as with aqueous sugar or alditol solutions.

If a low calorie gum is desired, a low caloric bulking agent can be used. Examples of low caloric bulking agents include, but are not limited to: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can also be used.

A variety of flavoring agents can be used, if desired. Flavoring agents like colorants are useful in chewing gum compositions to impart characteristics and to remove or mask undesired characteristics. In particular, the flavoring agent of the present invention should be capable of masking the unpleasant taste sensation associated with sildenafil citrate. In doing so, the flavoring agent increases the contact time of the chewing gum composition of the present invention in the oral cavity. In doing so, the chewing gum composition enhances the absorption and bioavailability of the sildenafil citrate component and prolongs the drug's therapeutic effects by gradually releasing the agent from the chewing gum composition.

The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents such as cocoa powder and heat-modified amino acids can be used as a flavoring agent within the present invention, and may be combined in any sensorially acceptable fashion.

Since sildenafil citrate at ambient conditions is a white or off-white crystalline powder that exhibits moderate water solubility (3.5 g/L), the chewing gum composition of the present invention will preferably include a emulsifier system to achieve the desired concentration of the medicament in the saliva.

The chewing gum composition of the present invention can be made utilizing manufacturing procedures known within the chewing gum arts. In general, chewing gum is manufactured by sequentially adding the various chewing gum ingredients to a commercially available mixer known in the art. After the initial ingredients have been thoroughly mixed, the gum mass is discharged from the mixer and shaped into the desired form such as by rolling into sheets and cutting into sticks, extruded into chunks or casting into pellets or balls.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent/sweetener. Further portions of the bulking agent/sweetener may then be added to the mixer thereafter. A flavoring agent is typically added with the final portion of the bulking agent/sweetener. A high-intensity sweetener is preferably added after the final portion of the bulking agent/sweetener and flavor have been added.

The entire mixing procedure typically takes from five to fifteen minutes, but longer mixing times may sometimes be required. Those skilled in the art will recognize that many variations of the above-described procedure may be followed.

In manufacturing the chewing gum composition of the present invention in particular, the medicament is mixed with the gum base, sweetener or sweetener mixture, and a flavoring agent. Preferably, the medicament is added early on in the mix. The smaller the amount of sildenafil used, the more necessary it becomes to preblend that particular ingredient to assume uniform distribution throughout the batch of gum.

Whether a preblend is used or not, in a preferred embodiment, the agent or medicament should be added within the first five minutes of mixing. Because the chewing gum composition of the present invention contains a water insoluble base, it enhances the gradual or controlled release of the medicament from the composition into the oral cavity. Thus, as the chewing gum composition of the present invention is chewed, the sildenafil citrate component will gradually dissipate, along with the sweeteners and flavor, during chewing.

Again, such gradual release enhances the absorption and bioavailability of the medicament from the oral cavity to the systemic system via the buccal or sublingual absorption routes. Additionally, the gradual release of sildenafil citrate from the chewing gum composition of the present invention, reduces or eliminates the gastroesophageal reflux side effect associated with the drug.

It is also preferable that the sildenafil citrate component of the present invention be first ground into fine particles to form a powder before being mixed with the gum base. The particle size of the sildenafil citrate component is preferably from about 0.1 microns to about 200 microns in diameter, more preferably from about 1 micron to about 50 microns in diameter.

In addition, prior to the sildenafil citrate powder being mixed with the gum base, the fine powder is preferably dissolved into a liquid or liquid mixture, which is preferably water-insoluble. This is done to ease incorporation of the drug into the gum base and to enhance its uniform distribution throughout the overall chewing gum composition. Examples of liquid or liquid mixtures suitable for use within the present invention include, but are not limited to, an alcohol, an edible oil, glycerin, ethylene glycol, propylene glycol, triacetin, tributyrin glycerol mono- or di-stearate, acetylated mono-glyceride of coconut oil combinations thereof, and other like materials.

The sildenafil citrate powder can be mixed with molten or softened gum base directly, or it can be pre-mixed with a gum base ingredient such as polyvinyl acetate, rosin esters, polyterpene, waxes, fats, and the like.

By providing a gradual release dosage form which can incorporate sildenafil citrate, the chewing gum composition of the present invention offers an advantage over the prior art because a greater amount of the drug is available to produce a therapeutic effect over an extended period of time. As mentioned above, the present invention also provides a delivery vehicle or dosage form that reduces or eliminates the gastroesophageal reflux side effect associated with the sildenafil citrate unlike other oral dosage forms. Further, the present invention contemplates not only treatment of male erectile dysfunction, but also the treatment of gastroparesis associated with diabetes, esophageal spasms, and dysphagia. The present invention offers a chewing gum composition that gradually releases sildenafil citrate such that the drug can be utilized to treat a variety of medical conditions rather than one condition in particular.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method for treating erectile dysfunction in an individual comprising the steps of:
   providing a chewing gum composition that includes a therapeutically effective amount of sildenafil citrate in the chewing gum composition; and
   chewing the chewing gum composition to cause the sildenafil citrate to be released from the chewing gum composition into the oral cavity of the individual.

2. The method of claim 1, wherein the chewing gum is chewed for at least 2 minutes.

3. The method of claim 1, wherein said therapeutically effective amount of sildenafil citrate is approximately 20 mg to about 100 mg.

4. The method of claim 1, wherein the method further includes the step of chewing the chewing gum composition for at least 30 minutes prior to engaging in a sexual activity.

5. A method of reducing esophageal spasms or dysphagia in an individual comprising the steps of:
   providing a chewing gum composition that includes a therapeutically effective amount of sildenafil citrate; and
   chewing the chewing gum composition to cause the sildenafil citrate to be released from the chewing gum composition into the oral cavity of the individual.

6. The method of claim 5, wherein the chewing gum is chewed for at least 2 minutes.

7. The method of claim 5, wherein said method further includes the step of chewing the chewing gum composition at least twice a day.

8. The method of claim 5, wherein the therapeutically effective amount of said sildenafil citrate is approximately 5 mg to about 100 mg.

9. A method of treating gastroparesis associated with diabetes comprising the steps of:
   providing a chewing gum composition including a therapeutically effective amount of sildenafil citrate; and
   chewing the chewing gum composition and thereby causing the sildenafil citrate to be released into the saliva.

10. The method of claim 9, wherein the therapeutically effective amount of said sildenafil citrate is approximately 5 mg to about 100 mg.

11. The method of claim 9, wherein the chewing gum is chewed for at least 2 minutes.

12. The method of claim 9, wherein said method further includes the step of chewing the gum at least twice a day.

13. A method of reducing or eliminating the gastroesophageal reflux side effect associated with orally administered sildenafil citrate comprising the steps of:
   providing a chewing gum composition that includes sildenafil citrate;
   chewing the chewing gum composition to cause the sildenafil citrate to be gradually released from the chewing gum composition into the oral cavity of the individual; and continuing to chew the chewing gum composition thereby causing said sildenafil citrate to enter the systemic system through the oral mucosa of the oral cavity via the buccal or sublingual absorption routes rather than the gastrointestinal tract.

14. The method of claim 13, wherein the chewing gum composition is chewed for at least 2 minutes.

15. A chewing gum composition comprising:

a water insoluble base portion;

a water soluble portion;

a therapeutically effective amount of a member selected from the group consisting of sildenafil, sildenafil citrate, derivatives thereof, and combinations thereof that is designed to be absorbed through the oral mucosa of an individual chewing the chewing gum;

a sweetener; and a flavor.

16. The chewing gum composition of claim 15, wherein said chewing gum composition comprises approximately 5 mg to about 100 mg of sildenafil citrate.

17. The chewing gum composition of claim 16, wherein said sildenafil citrate is a powder having a particle of size of approximately 0.1 microns to about 200 microns.

18. The chewing gum composition of claim 15, wherein said water insoluble base portion is a bubble gum base.

19. The chewing gum composition of claim 15 comprising a coating that surrounds a chewing gum center, the coating comprises sildenafil.

20. The chewing gum composition of claim 15 wherein a chewing gum coating surrounds a compressible excipient.

21. The chewing gum composition of claim 19 wherein the coating comprises a masking agent.

22. A method of producing a chewing gum composition comprising a therapeutically effective amount of sildenafil citrate comprising the steps of:

grinding the sildenafil citrate into a fine powder having a particle size of approximately 0.1 microns to about 200 microns;

mixing the sildenafil citrate powder with a liquid to form an incorporation vehicle; and mixing the incorporation vehicle with a chewing gum carrier so that the sildenafil citrate is released into the oral mucosa of an individual placing the chewing gum in their mouth, the chewing gum carrier comprising:

a water insoluble gum base portion;

a water soluble portion;

a sweetener; and a flavor.

23. The method of claim 22, wherein the therapeutically effective amount of sildenafil citrate is approximately 5 mg to about 100 mg.

24. The method of claim 22, wherein the liquid is a member selected from the group consisting of an alcohol, an edible oil, glycerin, ethylene glycol, propylene glycol, triacetin, tributyrin, glycerol mono- or di-stearate, acetylated mono-glyceride of coconut oil and combinations thereof.

25. A method of preparing a gum base comprises sildenafil citrate comprising the steps of:

grinding the sildenafil citrate into a fine powder; and incorporating the sildenafil citrate powder within a gum base to encapsulate the sildenafil citrate powder.

26. The method of claim 25, wherein a therapeutically effective amount of sildenafil citrate is incorporated in the gum base.

27. The method of claim 26, wherein the particle size of the sildenafil citrate powder is approximately 0.1 microns to about 200 microns.

28. A chewing gum composition comprising:

a water insoluble base portion;

a water soluble portion;

a therapeutically effective amount of a member selected from the group consisting of sildenafil, sildenafil citrate and combinations thereof;

a sweetener; and a flavor.

29. The chewing gum composition of claim 28, wherein said chewing gum composition comprises approximately 5 mg to about 100 mg of sildenafil citrate.

30. The chewing gum composition of claim 28, wherein said sildenafil citrate is a powder having a particle of size of approximately 0.1 microns to about 200 microns.

31. The chewing gum composition of claim 28, wherein said water insoluble base portion is a bubble gum base.

32. The chewing gum composition of claim 28, which includes a coating that surrounds a chewing gum center, the coating comprises sildenafil.

33. The chewing gum composition of claim 28, wherein a chewing gum coating surrounds a compressible excipient.

\* \* \* \* \*